United States Patent [19]

Smith

[11] Patent Number: 5,458,893
[45] Date of Patent: Oct. 17, 1995

[54] PROCESS FOR TREATING WATER-SOLUBLE DIETARY FIBER WITH BETA-GLUCANASE

[75] Inventor: John J. Smith, Hoffman Estates, Ill.

[73] Assignee: The Quaker Oats Company, Chicago, Ill.

[21] Appl. No.: 156,134

[22] Filed: Nov. 22, 1993

Related U.S. Application Data

[63] Continuation-in-part of Ser. No. 847,258, Mar. 6, 1992, abandoned.

[51] Int. Cl.$^6$ .......................................... A23L 1/10
[52] U.S. Cl. .................. 426/18; 426/28; 426/31; 426/549; 426/573; 426/590; 426/589; 426/580; 426/641
[58] Field of Search .................. 426/28, 18, 31, 426/549, 573, 590, 589, 580, 641

[56] References Cited

U.S. PATENT DOCUMENTS

| | | | |
|---|---|---|---|
| 4,448,790 | 5/1984 | Sarkki | 426/18 X |
| 4,996,063 | 2/1991 | Inglett | 426/61 |
| 5,082,673 | 1/1992 | Inglett | 426/21 |
| 5,106,640 | 4/1992 | Lehtomaki et al. | 426/436 |

FOREIGN PATENT DOCUMENTS 8908405  9/1989  WIPO.

OTHER PUBLICATIONS

*The Kirk–Othmer Encyclopedia of Chemical Technology:* Third Edition, vol. 9, pp. 195–199 (1980).
"Effects of Starch Particle Size and Protein Concentation on Breadmaking Performance": J. Lelievre, K. Lorenze, P. Meredith and D. Baruch; *Starch/Starke,* 39 (1987) Nr. 10, S. pp. 347–352.
"Novo Enzymes—Cereflo": *Advertising Brochure:* Jul., 1981.

*Primary Examiner*—Joseph Golian
*Attorney, Agent, or Firm*—Lars S. Johnson; Mart C. Matthews

[57] ABSTRACT

The present invention relates to an improved process for producing a beta-glucanase treated water-soluble dietary fiber composition wherein an aqueous dispersion of a gelatinized, milled, beta-glucan containing grain-based substrate is treated with an alpha-amylase under conditions which will hydrolyze said substrate and yield a soluble fraction and an insoluble fraction, separating said soluble fraction from said insoluble fraction, and recovering from said soluble fraction said water-soluble dietary fiber substantially free of water-insoluble fiber, wherein the improvement comprises treating beta-glucans released from the grain-based substrate with beta-glucanase, wherein the weight ratio of beta-glucanase to initial beta-glucan containing substrate is in the range of from about $4\times10^{-6}{:}1$ to about $2\times10^{-2{:}1}$ (beta-glucanase:grain-based substrate), and wherein the treatment of the beta-glucans with the beta-glucanase is carried out at a temperature in the range of from about 30° C. to about 60° C., for a period of time in the range of from about 5 to about 120 minutes, and at a pH in the range of from about 5 to about 7. The present invention further comprises dietary fiber compositions produced by the above-described process, edible food compositions containing the dietary fiber compositions produced by the above-described process, and a method for preparing said edible food compositions.

16 Claims, No Drawings

PROCESS FOR TREATING WATER-SOLUBLE DIETARY FIBER WITH BETA-GLUCANASE

This is a continuation-in-part of application(s) Ser. No. 07/847,258 filed on Mar. 6, 1992, now abandoned.

FIELD OF THE INVENTION

The present invention relates to a process for treating water-soluble dietary fiber with beta-glucanase. The present invention further relates to the product of said treatment process and a method for preparing edible compositions utilizing the product of said treatment process.

BACKGROUND OF INVENTION

Dietary fat intake has been associated with a number of undesired health problems such as obesity, cardiovascular disease, increased cholesterol levels, etc. Thus, there is a great desire to find edible ingredients which are capable of partially or totally replacing fats in foods, and a number of fat replacements are known in the art. However, there are a number of problems associated with many of these fat replacements. One such problem is that some fat replacements may not provide a final product having the same texture and/or mouthfeel as a product prepared with fat. For example, when certain fat replacements are used to prepare baked products, the final baked product is tougher, dryer (less moist) and has a lower volume than a product prepared with fat. Other examples of such problems include fat replacements which lack heat stability or exhibit undesirable physical effects on consumers, for example anal leakage.

Thus, a most desired fat replacement would mimic fats in all these areas, i.e., would provide products having the same or similar taste, feel, texture, heat stability and cooking properties as products prepared from fats, and yet would not possess or cause any of the undesirable properties or effects described above and would not have any additional undesirable physical effects of their own. Such is the case of the beta-glucanase treated water-soluble dietary fiber composition prepared in accordance with the present invention.

Alternatively, there are those who are unconcerned about fat in their diets and wish to maximize the mouthfeel and textural properties associated with fats. The beta-glucanase treated water-soluble dietary fiber compositions of the present invention, when used as a food additive instead of as a fat replacement, act in concert with any fats present in food products to amplify the texture and mouthfeel properties associated with such fats.

BACKGROUND ART

Enzymes have long been used in food processing, one example being the use of yeast for fermentation. Furthermore, it has been known that particular enzymes are useful for specific applications since at least the middle of the 19th century.

The use of the enzyme beta-glucanase in food processing is also known. The Kirk-Othmer Encyclopedia of Chemical Technology, Third Edition, Volume 9, pp. 195–199 (1980), teaches that beta-glucanase is a carbohydrase and "beta-glucanase from *Bacillus subtilis*, and *Asperillus niger*, attacks the 1,3-beta and 1,4-beta linkages in yeast cell walls and barley. The barley beta-glucans are solubilized at 60–65 decrees C, the temperature at which starch is gelatinized in mashing for beer production. At this temperature the beta-glucanase present in barley is destroyed; addition of microbial beta-glucanase reduces viscosity and facilitates filtration of the mash. " (See pages 198–199.) This reference also teaches, at p. 215, that beta-glucanase marketed as Cereflo™ 200 L (available from Novo Laboratories Inc., Wilton, Conn.), which is obtained from *Bacillus subtilis* and *Candida utilis*, "lowers beer or wort viscosity by degrading barley glucans to facilitate filtration; often found in varying amounts in *B. subtilis* amylase and protease preparations."

The art also teaches a process for preparing water-soluble dietary fiber compositions from oats. U.S. Pat. No. 4,996,063, issued Feb. 26, 1991 to Inglett, teaches preparing water-soluble dietary fiber compositions by treating an aqueous dispersion of a gelatinized, milled, oat substrate with an alpha-amylase under conditions which will hydrolyze the substrate and yield a soluble fraction and an insoluble fraction, separating said soluble fraction from said insoluble fraction, and recovering from said soluble fraction said water-soluble dietary fiber substantially free of water-insoluble fiber. These water-soluble dietary fiber compositions are useful as food ingredients, and are particularly useful as fat replacements, since in addition to providing a product having few or none of the undesirable properties of fats as described above, the compositions also provide soluble dietary fiber, which has been shown in Burkitt et al. [Lancet 2:1408–11 (1972)] to play a role in preventing certain large-intestine diseases, including cancer of the colon and diverticulitis. Furthermore, such soluble dietary fiber has been shown in the same study to lower serum cholesterol, and thus also provides a desired positive health benefits.

However, the water-soluble dietary fiber compositions prepared by the known process of the '063 patent can be improved upon. It has now been found that when the beta-glucans present in such water-soluble dietary fiber compositions are treated with beta-glucanase, the resulting composition provides unexpectedly improved fat mimicking properties when used as an ingredient in a food product over untreated water-soluble dietary fiber.

It is therefore an object of the present invention to provide a process for treating the beta-glucans released in the above-described known process for preparing water-soluble dietary fiber compositions with beta-glucanase.

It is also an object of the present invention to provide beta-glucanase treated water-soluble dietary fiber compositions prepared in accordance with the present invention which, when used as a food ingredient, provide products having improved fat mimicking properties when compared to corresponding products prepared with a water-soluble dietary fiber composition which has not been treated with beta-glucanase.

It is still another object of the present invention to provide edible compositions utilizing such dietary fiber compositions, preferably as a partial or total fat replacement, and a method for preparing said edible compositions.

These objects are accomplished by the invention described herein.

SUMMARY OF THE INVENTION

The present invention relates to an improved process for producing a beta-glucanase treated water-soluble dietary fiber composition wherein an aqueous dispersion of a gelatinized, milled, beta-glucan containing grain-based substrate is treated with an alpha-amylase under conditions which will hydrolyze said substrate and yield a soluble fraction and an insoluble fraction, separating said soluble fraction from said insoluble fraction, and recovering from said soluble fraction said water-soluble dietary fiber substantially free of water-insoluble fiber, wherein the improvement comprises treating beta-glucans released from the grain-based substrate with beta-glucanase, wherein the weight ratio of beta-glucanase to initial beta-glucan containing substrate is in the range of from about $4 \times 10^{-6}$:1 to about $2 \times 10^{-2}$:1 (beta-glucanase:grain-based substrate), and wherein the treatment of the beta-glucans with the beta-glucanase is carried out at a temperature in the range of from about 30° C. to about 60° C., for a period of time in the range of from about 5 to about 120 minutes, and at a pH in the range of from about 5 to about 7.

The present invention further comprises dietary fiber compositions produced by the above-described process, edible food compositions containing the dietary fiber compositions produced by the above-described process, and a method for preparing said edible food compositions.

DETAILED DESCRIPTION OF THE INVENTION

The present invention relates to an improvement to a known process for preparing a water-soluble dietary fiber composition. The general process parameters of the known process are as discussed in the '063 patent discussed above, the disclosure of which is incorporated herein. In the known process, an aqueous dispersion of a gelatinized, milled, oat substrate is treated with an alpha-amylase enzyme under conditions which will hydrolyze the substrate and yield a soluble fraction and an insoluble fraction. The soluble fraction is separated from the insoluble fraction, and the water-soluble dietary fiber is recovered from the soluble fraction substantially free of water-insoluble fiber. The water-soluble dietary fiber composition resulting from this process comprises beta-glucan, which is a water-soluble dietary fiber, and starch.

During the course of this known process, the oat substrate is hydrolyzed, which, among other things, causes beta-glucans to be released from the substrate. The present invention comprises an improvement over the known process wherein the released beta-glucans are treated with beta-glucanase enzyme. During such treatment, the beta-glucanase acts as a catalyst for the hydrolysis of any present beta-glucan molecules. This beta-glucanase treatment allows for a final beta-glucanase treated water-soluble dietary fiber composition which provides improved fat mimicking properties when used in the preparation of food items, as compared to untreated water-soluble dietary fiber compositions. These improvements include increased moisture retention, better mouthfeel, including creamier texture and less of a paste-like sensation, and increased volume in baked goods, as compared to untreated water-soluble dietary fiber compositions.

The substrate utilized in the '063 patent is limited to oat. However, in the present invention, any variety of milled, gelatinized beta-glucan containing grain-based substrate capable of undergoing hydrolysis in the presence of alpha-amylase may be used. In addition to the oat substrate used in the process of the '063 patent, examples of other useful grain-based substrates include, but are not limited to, barley, rice, and mixtures thereof. Oat, barley and mixtures thereof are preferred substrates, with oat being most preferred. The milled substrates may be in the form of bran, flour, or bran concentrates, or any other appropriate form known to those skilled in the art, with bran and flour being preferred and flour being most preferred.

The exact type or types of beta-glucans released will depend upon the type of grain-based substrate utilized. For example, oat and barley based substrates would release 1,4-beta- and 1,3-beta-glucans.

It is believed that the beta-glucanase utilized in the present invention may be obtained from any one of the various sources known to those skilled in the art. For example, beta-glucanase may be obtained from fungi sources, including but not limited to *Asperillus niger, Trichoderma longibrachiatum*, and *Penicillium emersonii*. The *Asperillus niger* can be obtained under the trade name Finizym™ from Novo Laboratories, and the *Trichoderma longibrachiatum* can be obtained under the trade name Laminex BG™ from Genencor International, located in Rolling Meadows, Ill. Beta-glucanase may also be obtained from bacteria, an example of which includes, but is not limited to, *Bacillus subtilis*. The beta-glucanase from *Bacillus subtilis* can be obtained under the trade name Cereflo™ 200 L, as already discussed herein. Beta-glucanase can also be obtained from yeast, examples of which include but are not limited to *Saccharomyces cerervisiae*. The preferred enzyme is Cereflo™200 L from the bacterium *Bacillus subtilis*.

In a typical method of obtaining beta-glucanase from such sources, an organism (e.g., fungi, bacteria or yeast) is grown in a medium in a containment vessel, such as a fermentation tank. An example of a useful medium is corn steep liquor. Depending upon the organism, the beta-glucanase may be secreted into the medium, whereupon it is extracted and purified, or it may be necessary to extract the beta-glucanase by rupturing the organism cell walls, after which the beta-glucanase may be purified.

It is believed that the beta-glucanase obtained from the various sources perform the same function, i.e., catalyze the hydrolysis of present beta-glucans, although each differing beta-glucanase will optimally perform this function under different conditions. For example, for beta-glucanase obtained from the fungus *Asperillus niger* the optimum temperature and pH are about 60° C. and about 5, respectively; for beta-glucanase obtained from the fungus *Penicillium emersonii* the optimum temperature and pH are about 70° C. and about 4, respectively; for beta-glucanase obtained from the fungus *Trichoderma longibrachiatum* the optimum temperature and pH are about 60° C. and about 5, respectively; and for beta-glucanase obtained from the bacteria *Bacillus subtilis* the optimum temperature and pH are about 50°–60° C. and about 7, respectively. The optimal enzymatic conditions for each specific enzyme are typically provided by the supplier of the enzyme.

The beta-glucanase can be added at any point in the process, i.e., together with the separately added alphaamylase; after the grain-based substrate is hydrolyzed with the alpha-amylase to yield a soluble and insoluble fraction; after separation of the soluble fraction from the insoluble fraction; at the process end; or at any other point. The beta-glucanase may even be added to a dried, water-soluble dietary fiber composition product prepared by the known process, provided the dried composition is re-hydrated. Re-hydration is necessary because the beta-glucanase acts to catalyze the hydrolysis of the present beta-glucans, and if no water is present, there can be no hydrolysis.

The beta-glucans released in the known process are treated with a sufficient amount of beta-glucanase for a sufficient length of time, and under sufficient temperature and pH conditions, to provide a beta-glucanase treated water-soluble dietary fiber composition which, when used as an additive or fat replacement in a food product, imparts the improved fat mimicking properties already described herein. Each of these individual process parameters is to a great degree dependent upon factors such as the type of substrate used, i.e., oat, barley, etc.; the source of enzyme; and the point in the known process at which the beta-glucans are treated with the enzyme. Thus, the optimal parameters for carrying out the process of the present invention will depend upon each of these factors.

Additionally, it is important that, through the manipulation of the process parameters, the beta-glucanase not be allowed to catalyze the hydrolysis of the beta-glucans to too great an extent. While not intending to be bound by theory, it is believed that during the beta-glucanase treatment the beta-glucan molecules are hydrolyzed to the point where they reach an optimal mixture comprised of beta-glucan molecules of varying chain lengths. It is believed this mix provides the final beta-glucanase treated water-soluble dietary fiber composition with desired properties when used as a food additive or fat substitute. Thus, the treatment of the beta-glucans should not be allowed to continue beyond the point at which the optimum mixture of beta-glucan molecule chain lengths are obtained.

The amount of beta-glucanase used in the process of the present invention can be expressed as the weight ratio of beta-glucanase used for treatment to the amount of initial grain-based substrate used in the process. The weight ratio of beta-glucanase to initial beta-glucan containing grain-based substrate is in the range of from about $4\times10^{-6}:1$ to about $2\times10^{-2}:1$, preferably from about $4\times10^{-5}:1$ to about $8\times10^{-3}:1$ (beta-glucanase:grain-based substrate). In a preferred example, when oat flour is used as a substrate and Cereflo™ 200 L is the enzyme source, the weight ratio of beta-glucanase to oat flour will be in the range of from about $2\times10^{-4}:1$ to about $8\times10^{-3}:1$, preferably from about $4\times10^{-4}:1$ to about $4\times10^{-3}:1$ (beta-glucanase:oat flour). In another preferred example, when barley flour is used as a substrate and Cereflo™ 200 L is the enzyme source, the weight ratio of beta-glucanase to barley flour will be in the range of from about $2\times10^{-4}:1$ to about $8\times10^{-3}:1$, preferably from about $4\times10^{-4}:1$ to about $4\times10^{-3}:1$ (beta-glucanase:barley flour).

As already stated herein, the time of actual treatment of the released beta-glucans with beta-glucanase will depend upon the type of substrate and enzyme utilized, as well as the point in the process at which the treatment occurs. For example, if the beta-glucanase is added to the process together with the separately added alpha-amylase, a longer treatment time may be required than if the beta-glucanase is added to the process following the separation of the water-soluble dietary fiber from the water-insoluble dietary fiber. This is because the beta-glucans are released from the grain substrate over a period of time, and the beta-glucanase can more efficiently catalyze the hydrolysis of beta-glucan molecules after they are released from the substrate. Thus, the rate of hydrolysis of the substrate has a rate-limiting effect upon the hydrolysis of the beta-glucans. In contrast, if the beta-glucans are treated with beta-glucanase following separation of the soluble fiber from the insoluble fiber, then the beta-glucans have already been released and are free for hydrolysis, without the rate-limiting effect of the hydrolysis of the substrate.

Preferably the beta-glucans are treated by the addition of beta-glucanase in conjunction with the alpha-amylase to the milled, gelatinized grain-based substrate. This is because while there is some rate-limiting effect, it is not significant in comparison to the convenience and efficiency of adding the two enzymes together. When beta-glucanase is added with the alpha-amylase, treatment is carried out for a period of time in the range of from about 5 minutes to about 120 minutes, preferably from about 30 to about 90 minutes. When beta-glucanase is added after hydrolysis of the substrate to yield the water-soluble and water-insoluble dietary fiber fractions, treatment is carried out for a period of time in the range of from about 5 minutes to about 120 minutes, preferably from about 30 minutes to about 90 minutes. When beta-glucanase is added after the separation of the water-soluble dietary fiber fraction from the water-insoluble fraction, treatment is typically carried out for a period of time in the range of from about 5 minutes to about 120 minutes, preferably from about 30 minutes to about 90 minutes. If the beta-glucans are treated with beta-glucanase after completion of the known process, treatment is typically carried out for a period of time in the range of from about 5 minutes to about 120 minutes, preferably from about 45 minutes to about 90 minutes.

Care must be taken to avoid excessive starch hydrolysis in the process of the present invention due to alpha-amylase attack. If such excessive starch hydrolysis does occur, then the improvements described herein will not be realized. This excessive starch hydrolysis is avoided by taking care to limit the amount of alpha-amylase utilized in the process of the present invention. The sources of alpha-amylase are the separately added alpha-amylase used to prepare the water-soluble dietary fiber composition and alpha-amylase present as a contaminant in some beta-glucanase samples.

The amount of alpha-amylase which can be utilized in the present invention will be dependent upon the source of alpha-amylase. The alpha-amylase levels disclosed in the '063 for its process are useful in the process of the present invention. If the teachings of the '063 patent are followed and if care is taken to avoid using a beta-glucanase sample contaminated with alpha-amylase, then the excessive starch hydrolysis can be avoided. Furthermore, one skilled in the art will appreciate when the alpha-amylase levels are too high by observing the failure of the final beta-glucanase treated water-soluble dietary fiber composition to exhibit the performance improvements described herein.

The beta-glucanase must be incubated, i.e., maintained at an optimum temperature, during the treatment period. Of course, as discussed before, the optimum temperature will depend upon the enzyme source and the type or types of beta-glucans being treated. Other factors to consider are the effect of the temperature upon the alpha-amylase and the grain-based substrate. Typically, when beta-glucanase is added with the alpha-amylase, treatment is carried out at a temperature in the range of from about 30° C. to about 60° C., preferably from about 40° C. to about 50° C. When beta-glucanase is added after the hydrolysis of the grain-based substrate to yield the water-soluble and water-insoluble dietary fiber fractions, treatment is carried out at a temperature in the range of from about 30° C. to about 60° C., preferably from about 40° C. to about 50° C. When beta-glucanase is added after the separation of the water-soluble dietary fiber fraction from the water-insoluble fraction, treatment is carried out at a temperature in the range of from about 30° C. to about 60° C., preferably from about 40° C. to about 50° C. If the beta-glucans are treated with beta-glucanase after completion of the known process, but prior to drying, treatment is carried out at a temperature in the range of from about 30° C. to about 60° C., preferably from about 40° C. to about 50° C.

As with the other process parameters, the pH at which treatment occurs is dependent upon the point at which treatment occurs, the type of substrate, and the source of beta-glucanase. Consideration must also be given to the effect of pH on the alpha-amylase if the beta-glucanase and alpha-amylase are added together. Typically, for beta-glucanase derived from bacteria such as Cereflo™ 200 L, the pH is maintained in the range of from about 5 to about 7, preferably from about 5 to about 6, when beta-glucanase is added with the alpha-amylase; from about 5 to about 7, preferably from about 5 to about 6 when beta-glucanase is added after the hydrolysis of the grain-based substrate to yield the water-soluble and water-insoluble dietary fiber fractions; and from about 5 to about 7, preferably from about 5 to about 6 when beta-glucanase is added after the separation of the water-soluble dietary fiber fraction from the water-insoluble fraction. If treatment occurs after completion of the known process, but prior to drying, the pH is maintained in the range of from about 5 to about 7, preferably from about 5 to about 6.

If necessary, the pH may be adjusted by any method known to those skilled in the art. Typical food grade acids useful for adjusting pH include, but are not limited to, phosphoric acid, citric acid, hydrochloric acid, adipic acid, malic acid, and fumaric acid, with phosphoric acid and citric acid being preferred and phosphoric acid being most preferred.

The length of time of the treatment is controlled by inactivating the beta-glucanase after the desired treatment period has been achieved. The beta-glucanase may be inactivated by any method known to those skilled in the art, giving consideration to other factors such as the source of beta-glucanase used and the point in the process at which the beta-glucans are treated with the beta-glucanase. For example, if the beta-glucanase is added to the process in conjunction with the alpha-amylase, care must be taken to avoid inadvertently inactivating the alpha-amylase before it fulfills its function as a catalyst for the hydrolysis of the substrate. Examples of useful methods of inactivating the beta-glucanase include, but are not limited to, heat treatment of the slurry, raising or lowering the pH of the slurry, and/or a combination of both. The preferred method of inactivating the beta-glucanase is by heating the slurry to a temperature greater than about 90° C. for a corresponding length of time in the range of from about 5 minutes to about 45 minutes, preferably from about 10 minutes to about 20 minutes, respectively.

As already stated herein, the beta-glucanase treatment may be carried out even after the known process is completed and a dried, finished water-soluble dietary fiber composition product is obtained. Furthermore, this may occur at almost any time after completion of the known process, i.e., hours, days, weeks, etc., provided there is no deterioration of the fiber composition product. When treatment is carried out in this manner, a preferred process in accordance with the present invention comprises: (a) preparing an aqueous suspension comprising the water-soluble dietary fiber composition recovered from milled products of beta-glucan containing grain-based substrates after enzymatic hydrolysis with alpha-amylase of the milled products in accordance with the known process already discussed herein; (b) preparing a slurry by combining beta-glucanase with the aqueous suspension; (c) incubating the slurry; and (d) inactivating the beta-glucanase.

The aqueous suspension contains from about 10% to about 40%, preferably from about 23% to about 27% by weight of water-soluble dietary fiber recovered from milled beta-glucan containing grain-based substrates after enzymatic hydrolysis with alpha-amylase. The aqueous suspension is preferably maintained at a temperature in the range of from about 10° C. to about 60° C., preferably from about 15° C. to about 30° C.

The aqueous suspension is typically formed by adding the water-soluble dietary fiber to water, followed by mixing. The mixing is preferably accomplished by stirring or blending, and is preferably carried out for a length of time sufficient to provide for a thorough distribution of the ingredients, typically from about 30 seconds to about 300 seconds, more typically from about 30 seconds to about 120 seconds. By thorough distribution, it is meant that the fiber tends to be dispersed evenly throughout the water, without a significant tendency to be concentrated in any particular region of the water.

After the aqueous suspension is prepared, beta-glucanase, preferably Cereflo™ 200 L, is added to the suspension to form a slurry. The beta-glucanase is added in amounts sufficient to enzymatically react with the water-soluble dietary fiber to provide a beta-glucanase treated water-soluble dietary fiber composition which, when used as an additive or fat replacement in a food product, imparts improved properties such as increased moisture retention, better mouthfeel, increased volume in baked goods, etc., as compared to food products prepared with untreated water-soluble dietary fiber compositions. Typically the slurry comprises from about 0.005% to about 0.2%, preferably from about 0.01% to about 0.1% by weight beta-glucanase.

Following addition of the beta-glucanase, the slurry is mixed, preferably by blending and/or stirring, and preferably for a length of time sufficient to allow for a substantially uniform distribution of the beta-glucanase throughout the slurry, more preferably for about 15 seconds to about 120 seconds, still more preferably from about 30 seconds to about 60 seconds. By "substantially uniform distribution" it is meant that the beta-glucanase tends to be distributed throughout the entire slurry, without a significant tendency to be concentrated in any particular region of the slurry.

After being prepared, the slurry is incubated, preferably under conditions sufficient to allow the beta-glucanase to catalyze the hydrolysis of the beta-glucans present in the slurry. The slurry is preferably incubated at a temperature of from about 30° C. to about 60° C., more preferably from about 40° C. to about 50° C., for a corresponding length of time in the range of from about 5 minutes to about 120 minutes, more preferably from about 45 minutes to about 90 minutes, respectively. The pH of the slurry containing the preferred Cereflo™ 200 L enzyme is preferably maintained in the range of from about 5.0 to about 7.0, more preferably from about 5.0 to about 6.0.

Following incubation, the beta-glucanase is inactivated. When the preferred Cereflo™ 200 L enzyme is used, it is inactivated by heating the slurry to a temperature in excess of about 90° C. for a corresponding length of time in the range of from about 5 minutes to about 45 minutes, preferably from about 10 minutes to about 20 minutes, respectively.

The product resulting from the process of the present invention, regardless of the point of beta-glucanase treatment, is a beta-glucanase treated water-soluble dietary fiber composition which is colorless, white and smooth textured, and devoid of inherent undesirable color, flavor and grittiness. These physical features make this product useful as a food ingredient, and particularly as a fat replacement.

The present invention further comprises edible compositions comprising one or more edible ingredients and the beta-glucanase treated water-soluble dietary fiber product of the above-described process, as well as a method for preparing said edible compositions. Said edible compositions are typically prepared by combining said dietary fiber product with the edible ingredients, preferably food or food products. While in no way intending to be an exhaustive list, or in any way limiting, examples of food and food products useful in the present invention include but are not limited to: meats and meat containing products such as sausages, hot dogs, hams, lunchmeats, modified raw meat, and other processed meats and meat products; dairy products such as ice cream, sour cream, cheeses and cheese foods, cottage cheese, butter, yogurt, cream, whipped cream, milk and milk containing products such as milk shakes and malteds; grain-based foods such as noodles and pasta; baked goods, doughs and dry mixes for preparing baked goods, and fillings for baked goods such as breads, biscuits, rolls, muffins, cakes, doughnuts, puffed pastries, cookies, crackers, cheese cakes, and griddle products such as pancakes, waffles and french toast; condiments such as barbecue sauce, salad dressing, mayonnaise, spreads, peanut butter, mustard, catsup, margarine, dessert toppings such as hot fudge and whipped topping; soups, gravies and sauces such as white sauce, borealis, tartar, bernaise, and pasta sauces such as alfredo, marinaro and tomato; beverages such as malt beverages, flavored and unflavored carbohydrate-containing isotonic beverages, carbonated beverages and dietary beverages; juices and juice drinks; snack foods such as extruded snacks, pretzels and potato chips; confectionery items such as icings and frostings, candies, chocolate and marshmallows; desserts such as gelatins and puddings; egg substitutes; dry mixes for preparing foods and food products such as pancake mix, waffle mix, beverage mix, etc.; and frozen and solidified foods such as frozen baked goods, frozen dinners, frozen dough and frozen novelties including frozen desserts. Processed meat and meat products, dairy products, baked goods, sauces and gravies, and frozen instant dough are preferred.

In the method of preparing said edible compositions, the beta-glucanase treated water-soluble dietary fiber is added in the manner in which ingredients are typically added for the particular type of product being prepared. For example, when added to bread, all that may be required is the addition of the beta-glucanase treated water-soluble dietary fiber to the dough mix. However, when used in cheese or cheese foods, additional process steps may be necessary to incorporate the fiber in the cheese.

When used as an additive or ingredient in an edible composition, the beta-glucanase treated water-soluble dietary fiber of the present invention typically comprises from about 0.1% to about 40.0%, preferably from about 0.1% to about 5.0% by weight of the total edible composition. For specific products, the beta-glucanase treated product of the process of the present invention typically comprises from about 0.3% to about 1.3%, preferably from about 0.6% to about 1.0% by weight biscuit dough; from about 0.3% to about 1.3%, preferably from about 0.6% to about 1.0% by weight cookie dough; from about 0.3% to about 1.3%, preferably from about 0.7% to about 1.0% by weight of a muffin; from about 0.1% to about 0.4%, preferably from about 0.2% to about 0.3% by weight of a dinner roll; from about 0.2% to about 1.2%, preferably from about 0.6% to about 1.0% by weight of a cake; from about 0.1% to about 0.4%, preferably from about 0.2% to about 0.3% by weight of bread; from about 0.1% to about 0.5%, preferably from about 0.3% to about 0.4% by weight of a pancake; from about 0.1% to about 0.4%, preferably from about 0.2% to about 0.3% by weight of yogurt; from about 0.2% to about 1.0%, preferably from about 0.5% to about 0.8% by weight of ice cream; from about 0.5% to about 4.0%, preferably from about 1.0% to about 2.0% by weight salad dressing; from about 0.8% to about 4.0%, preferably from about 2.0% to about 3.2% by weight of a spread; and from about 0.1% to about 0.4%, preferably from about 0.2% to about 0.3% by weight of a doughnut.

In a preferred mode, the beta-glucanase treated water-soluble dietary fiber product of the present invention is used as either a partial or total fat replacement. When used as a fat replacement, the concentration of the beta-glucanase treated water-soluble dietary fiber is generally higher than when used as a separate ingredient in addition to fats, and typically comprises from about 2% to about 50%, preferably from about 4% to about 40% by weight of the edible composition. For specific products, the beta-glucanase treated product of the process of the present invention typically comprises from about 2.6% to about 5.2%, preferably from about 2.9% to about 3.5% by weight cookie dough; from about 2.2% to about 4.4%, preferably from about 2.4% to about 3.0% by weight of a baked biscuit; from about 2.5% to about 5.2%, preferably from about 2.8% to about 3.4% by weight of a muffin; from about 0.7% to about 1.4%, preferably from about 0.8% to about 1.0% by weight of a dinner roll; from about 2.4% to about 4.8%, preferably from about 2.6% to about 3.2% by weight of a cake; from about 0.8% to about 1.6%, preferably from about 0.9% to about 1.1% by weight of bread; from about 1.0% to about 2.0%, preferably from about 1.1% to about 1.4% by weight of a pancake; from about 0.8% to about 1.6%, preferably from about 0.9% to about 1.1% by weight of yogurt; from about 2.0% to about 4.0%, preferably from about 2.2% to about 2.7% by weight of ice cream; from about 1.0% to about 6.0%, preferably from about 4.0% to about 5.0% by weight salad dressing; from about 15% to about 50%, preferably from about 25% to about 40% by weight of a low fat spread; and from about 0.8% to about 1.6%, preferably from about 0.9% to about 1.1% by weight of a doughnut.

The present invention is further illustrated, but not limited by, the following examples.

EXAMPLES

Example 1

The following is a method for preparing a water-soluble, dietary fiber composition obtained from a gelatinized, milled, oat substrate and treating said dietary fiber composition with beta-glucanase.

One hundred grams (dry basis) of oat flour (The Quaker Oats Company, Cedar Rapids, Iowa) was slurried in 400 ml of water containing 25 ppm of calcium (0.09 g/l $CaCl_2.2H_2O$) and gelatinized by passage through a steam injection cooker at 138°–143° C. (30–40 psi steam pressure). The gelatinized mixture is collected in a container, and the pH is adjusted to 7 with 1.0N NaOH. Alpha-amylase (as "Enzeco Thermolase" from the Enzyme Development Div., Biddle Sawyer Corporation, New York, N.Y.) is added to the mixture at 95° C. in an amount sufficient to provide 24 units of amylase activity per gram of oat flour, where 1 unit of amylase activity is the amount of enzyme required to hydrolyze 10 mg of starch per minute under specified conditions [Enzyme Development Div., Biddle Sawyer Corp., New York, N.Y., Technical Bulletin No. 20 (Revised July/1986)]. After 20 minutes of stirring at 95° C., the starch is liquefied, and the enzyme is inactivated by passing the mixture through the steam injection cooker. the mixture is allowed to cool to about 70° C., and is centrifuged for 30 minutes at 5000 RPM. The water-soluble fiber product in the supernatant solution is recovered by decanting the solution and freeze-drying. The insoluble residue obtained from centrifuging is removed and air-dried.

Twenty five grams (dry basis) of this recovered water-soluble dietary fiber product is added to 75 grams of tap water at 25° C. to prepare a mixture. The mixture is blended for 1 minute using a hand-held blender to form a slurry. The pH of the slurry is adjusted to 6.5 with phosphoric acid. 0.01 grams of beta-glucanase (Cereflo™ 200 L) is added to the slurry, and the slurry is blended using a hand-held blender for 30 seconds. The beta-glucanase is substantially free of alpha-amylase. The slurry is then incubated for a period of 1 hour at a temperature of 45° C. Following incubation, enzyme activity is terminated by heating the slurry for 10 minutes at 90° C.

The slurry can be used as a food ingredient or fat substitute in food products.

Example 2

A process similar to the process in Example 1 wherein 10 grams (dry basis) of the recovered water-soluble dietary fiber product is added to 90 grams of tap water at 30° C. to prepare a mixture. The mixture is blended for 30 seconds using a hand-held blender to form a slurry. The pH of the slurry is adjusted to 5.5 with citric acid. 0.005 grams of beta-glucanase (Cereflo™ 200 L) is added to the slurry, and the slurry is blended using a hand-held blender for 15 seconds. The beta-glucanase is substantially free of alpha-amylase. The slurry is then incubated for a period of 2 hours at a temperature of 30° C. Following incubation, enzyme activity is terminated by heating the slurry for 5 minutes at 90° C.

The slurry can be used as a food ingredient or fat substitute in food products.

Example 3

A process similar to the process in Example 1 wherein 40 grams (dry basis) of the recovered water-soluble dietary fiber product is added to 60 grams of tap water at 60° C. to prepare a mixture. The mixture is blended for 5 minutes using a hand-held blender to form a slurry. The pH of the slurry is adjusted to 6.5 with malic acid. 0.2 grams of beta-glucanase (Cereflo™ 200 L) is added to the slurry, and the slurry is blended using a hand-held blender for 2 minutes. The beta-glucanase is substantially free of alpha-amylase. The slurry is then incubated for a period of 10 minutes at a temperature of 60° C. Following incubation, enzyme activity is terminated by heating the slurry for 45 minutes at 90° C.

The slurry can be used as a food ingredient or fat substitute in food products.

Example 4

The following is a method for preparing a water-soluble, dietary fiber composition obtained from a gelatinized, milled, oat substrate and treating said dietary fiber composition with beta-glucanase.

One hundred grams (dry basis) of oat flour (The Quaker Oats Company, Cedar Rapids, Iowa) is slurried in 400 ml of water containing 25 ppm of calcium (0.09 g/1 $CaCl_2.2H_2O$) and gelatinized by passage through a steam injection cooker at 138°–143° C. (30–40 psi steam pressure). The gelatinized mixture is collected in a container, and the pH is adjusted to 6.5 with phosphoric acid. The mixture is then cooled to 45° C. Beta-glucanase (Cereflo™ 200 L) is added to the mixture at 40° C. in an amount sufficient to provide 0.8 units of glucanase activity per gram of oat flour, where 1 unit of glucanase activity is the amount of enzyme required to degrade barley beta-glucan to reducing carbohydrates with a reduction power corresponding to 1 micromole of glucose per minute under specified conditions [Novo Laboratories, Danbury, Conn., Cereflo™ product specification sheet.] The beta-glucanase is substantially free of alpha-amylase. The beta-glucanase containing mixture is stirred at a temperature of 45° C. for a period of 60 minutes, after which the mixture temperature is raised to 95° C. Alpha-amylase (as "Enzeco Thermolase" from the Enzyme Development Div., Biddle Sawyer Corporation, New York, N.Y.) is then added to the mixture at 95° C. in an amount sufficient to provide 24 units of amylase activity per gram of oat flour, where 1 unit of amylase activity is the amount of enzyme required to hydrolyze 10 mg of starch per minute under specified conditions [Enzyme Development Div., Biddle Sawyer Corp., New York, N.Y., Technical Bulletin No. 20 (Revised July/1986)]. The mixture is then stirred by a hand mixer at a temperature of 95° C. for a period of 20 minutes. During this period the beta-glucanase enzyme is rendered inactive. After stirring, the starch is liquefied, and the alpha-amylase enzyme is inactivated by passing the mixture through the steam injection cooker. The mixture is allowed to cool to about 70° C., and is centrifuged for 30 minutes at 5000 RPM. The water-soluble fiber product in the supernatant solution is recovered by decanting the solution and freeze-drying. The insoluble residue obtained from centrifuging is removed and air-dried.

The recovered beta-glucanase treated water-soluble fiber product can be used as a food ingredient or fat substitute in food products.

Example 5

The following is a method for preparing a water-soluble, dietary fiber composition obtained from a gelatinized, milled, barley substrate and treating said dietary fiber composition with beta-glucanase.

One hundred grams (dry basis) of barley flour (The Quaker Oats Company, Cedar Rapids, Iowa) is slurried in 400 ml of water containing 25 ppm of calcium (0.09 g/1 $CaCl_2.2H_2O$) and gelatinized by passage through a steam injection cooker at 138°–143° C. (30–40 psi steam pressure). The gelatinized mixture is collected in a container, and the pH is adjusted to 7 with 1.0N NaOH. Alpha-amylase (as "Enzeco Thermolase" from the Enzyme Development Div., Biddle Sawyer Corporation, New York, N.Y.) is added to the mixture at 95° C. in an amount sufficient to provide 24 units of amylase activity per gram of barley flour, where 1 unit of amylase activity is the amount of enzyme required to hydrolyze 10 mg of starch per minute under specified conditions [Enzyme Development Div., Biddle Sawyer Corp., New York, NY, Technical Bulletin No. 20 (Revised July/1986)]. After 20 minutes of stirring at 95° C., the starch is liquefied, and the enzyme is inactivated by passing the mixture through the steam injection cooker. the mixture is allowed to cool to about 70° C., and is centrifuged for 30 minutes at 5000 RPM. The water-soluble fiber product in the supernatant solution is recovered by decanting the solution and freeze-drying. The insoluble residue obtained from centrifuging is removed and air-dried.

Twenty five grams (dry basis) of this recovered water-soluble dietary fiber product is added to 75 grams of tap water at 25° C. to prepare a mixture. The mixture is blended for 1 minute using a hand-held blender to form a slurry. The pH of the slurry is adjusted to 6.5 with phosphoric acid. 0.01 grams of beta-glucanase (Cereflo™ 200 L) is added to the slurry, and the slurry is blended using a hand-held blender for 30 seconds. The beta-glucanase is substantially free of alpha-amylase. The slurry is then incubated for a period of 1 hour at a temperature of 45° C. Following incubation, enzyme activity is terminated by heating the slurry to 90° C. for 10 minutes.

The slurry can be used as a food ingredient or fat substitute in food products.

Example 6

The following is a recipe for preparing no-fat-added muffins containing the beta-glucanase treated water-soluble dietary fiber composition prepared in example 1:

| Ingredient | Wt. % |
| --- | --- |
| Cake Flour | 32.11 |
| Sugar | 25.00 |
| Water | 21.32 |
| Beta-Glucanase Treated Water-Soluble Dietary Fiber | 15.81 |
| Non-Fat Dried Milk | 2.20 |
| Dried Whole Egg | 2.02 |
| Salt | 0.94 |
| Sodium Aluminum Phosphate | 0.30 |
| Baking Soda | 0.30 |
| TOTAL | 100.00 |

One hundred grams of muffin batter is prepared as follows:

Cream the sugar with 3.15 grams of the beta-glucanase treated water-soluble dietary fiber for 3 minutes at low speed using a 5-quart Hobart™ mixer. The beta-glucanase is substantially free of alpha-amylase. Separately combine the dry ingredients and mix for 2 minutes at low speed. Combine the creamed sugar and the dried mix and mix for 2 minutes at low speed, Add half the water and the remaining beta-glucanase treated water-soluble dietary fiber and mix for 1 minute on low speed, Add the remaining water and mix for 3 minutes on high speed.

The resulting muffin batter is baked in a muffin pan at 190° C. for 30 minutes,

Example 7

The following is a recipe for preparing a no-fat-added Italian salad dressing containing the beta-glucanase treated water-soluble dietary fiber composition prepared in example 1:

| Ingredient | Wt. % |
| --- | --- |
| Water | 35.50 |
| Beta-Glucanase Treated Water-Soluble Dietary Fiber | 26.00 |
| Vinegar | 22.00 |
| Butter Milk Powder | 8.00 |
| Sugar | 5.00 |
| Salt | 1.80 |
| Onion Powder | 0.50 |
| Garlic Powder | 0.40 |
| Paprika | 0.30 |

-continued

| Ingredient | Wt. % |
| --- | --- |
| Xanthan Gum | 0.30 |
| Oregano Leaves | 0.10 |
| Basil Leaves | 0.10 |
| TOTAL | 100.00 |

One hundred grams of salad dressing is prepared as follows:

Combine water, beta-glucanase treated water-soluble dietary fiber, and vinegar in a 5-quart bowl and stir. Separately combine the dry ingredients. The beta-glucanase in substantially free of alpha-amylase. Add the dry ingredients to the water/dietary fiber/vinegar mixture and combine using a spoon. Blend the resulting mixture at low speed using a Braun™ hand blender until lump free.

Example 8

The following is a recipe for preparing a no-fat-added ice cream containing the beta-glucanase treated water-soluble dietary fiber composition prepared in example 1:

| Ingredient | Wt. % |
| --- | --- |
| Water | 46.80 |
| Heavy Cream | 16.50 |
| Sugar | 12.00 |
| Non-Fat Dry Milk | 11.00 |
| Beta-Glucanase Treated Water-Soluble Dietary Fiber | 8.00 |
| Corn Syrup Solids | 4.00 |
| Vanilla | 1.40 |
| Stabilizer | 0.30 |
| TOTAL | 100.00 |

One hundred grams of ice cream is prepared as follows:

Combine non-fat dried milk, cream and half the water, mix well and set aside. Separately combine and blend the dry ingredients with a spoon. The beta-glucanase is substantially free of alpha-amylase. Preheat the remaining water to 60° C and slowly blend the combined dry ingredients into the remaining preheated water at high speed using a 5-quart Hobart™ mixer. Combine the non-fat dried milk/cream/water mixture with the water/dry ingredients mixture, place in a hot water bath, and heat to 70° C. with agitation. Add flavors and colors, mix well and freeze.

What is claimed is:

1. In a process for producing a beta-glucanase treated water-soluble dietary fiber composition wherein an aqueous dispersion of a gelatinized, milled, beta-glucan containing grain is treated with an alpha-amylase under conditions which will hydrolyze said grain and yield a soluble fraction and an insoluble fraction, separating said soluble fraction from said insoluble fraction, and recovering from said soluble fraction said water-soluble dietary fiber substantially free of water-insoluble fiber, wherein the improvement comprises treating beta-glucans released from the grain with beta-glucanase, wherein the weight ratio of beta-glucanase to initial beta-glucan containing grain is in the range of from about $4 \times 10^{-6}:1$ to about $2 \times 10^{-2}:1$ (beta-glucanase:grain), and wherein the treatment of the beta-glucans with the beta-glucanase is carried out at a temperature in the range of from about 30° to about 60° C., for a period of time in the range of from about 5 to about 120 minutes, and at a pH in the range of from about 5 to about 7.

2. A process according to claim 1 wherein the beta-glucans are treated by the addition of beta-glucanase to the aqueous dispersion of gelatinized, milled beta-glucan containing grain, and wherein the beta-glucan containing grain is selected from the group consisting of oat flour, oat bran, barley flour, barley bran, and mixtures thereof.

3. A process according to claim 1 wherein the beta-glucans are treated by the addition of beta-glucanase after the soluble fraction is separated from the insoluble fraction.

4. A process according to claim 2 wherein the beta-glucan containing grain is oat flour.

5. A process according to claim 4 wherein the beta-glucanase is derived from a bacterial source.

6. A process according to claim 5 wherein the beta-glucanase is derived from *Bacillus subtilis*.

7. A process according to claim 6 wherein the weight ratio of beta-glucanase to beta-glucan containing grain is in the range of from about $2\times10^{-4}:1$ to about $8\times10^{-3}:1$.

8. A process according to claim 7 wherein the beta-glucanase is inactivated by raising its temperature to at least about 90° C. for a length of time in the range of from about 5 minutes to about 45 minutes.

9. A beta-glucanase treated dietary fiber product produced by the process of claim 1.

10. An edible composition comprising edible ingredients and a beta-glucanase treated water-soluble dietary fiber composition ingredient, wherein said beta-glucanase treated water-soluble dietary fiber composition is prepared by a method comprising treating an aqueous dispersion of a gelatinized, milled, beta-glucan containing grain with an alpha-amylase under conditions which will hydrolyze said grain and yield a soluble fraction and an insoluble fraction, separating said soluble fraction from said insoluble fraction, and recovering from said water-soluble dietary fiber substantially free of water-insoluble fiber, wherein beta-glucans released from the grain are treated with beta-glucanase, wherein the weight ratio of beta-glucanase to initial beta-glucan containing grain is in the range of from about $4\times10^{-6}:1$ to about $2\times10^{-2}:1$ (beta-glucanase:grain, and wherein the treatment of the beta-glucans with the beta-glucanase is carried out at a temperature in the range of from about 30° to about 60° C., for a period of time in the range of from about 5 to about 120 minutes, and at a pH in the range of from about 5 to about 7.

11. An edible composition according to claim 10 wherein said beta-glucanase treated water-soluble dietary fiber composition ingredient is an additive and comprises from about 0.1% to about 40% by weight of the total edible composition.

12. An edible composition according to claim 11 wherein the edible ingredients comprise food and/or food products selected from the group consisting of processed meats and meat containing products; dairy products; baked goods, doughs, fillings for baked goods, and griddle products; condiments; soups, gravies and sauces; beverages; snack foods; confectionery items; desserts; egg substitutes; dry mixes; and frozen and solidified foods.

13. An edible composition according to claim 12 wherein the food and/or food product is a muffin and wherein the beta-glucanase treated water-soluble dietary fiber composition ingredient comprises from about 0.3% to about 1.3% by weight of the total edible composition.

14. An edible composition according to claim 10 wherein said beta-glucanase treated water-soluble dietary fiber composition ingredient is a partial or total fat replacement and comprises from about 2% to about 50% by weight of the total edible composition.

15. An edible composition according to claim 14 wherein the edible ingredients comprise food and/or food products selected from the group consisting of meats and meat containing products; dairy products; baked goods, doughs and dry mixes for preparing baked goods, fillings for baked goods, and griddle products; condiments; soups, gravies and sauces; beverages; snack foods; confectionery items; desserts; egg substitutes; dry mixes; and frozen and solidified foods.

16. An edible composition according to claim 15 wherein the food and/or food product is a muffin and wherein the beta-glucanase treated water-soluble dietary fiber composition ingredient comprises from about 2.5% to about 5.2% by weight of the total edible composition.

* * * * *